(12) United States Patent
Hidaka et al.

(10) Patent No.: US 6,180,828 B1
(45) Date of Patent: Jan. 30, 2001

(54) CATALYSTS FOR PRODUCING METHYLAMINES AND METHODS FOR PRODUCING METHYLAMINES USING THE SAME

(75) Inventors: Toshio Hidaka; Katsumi Higuchi; Nobuyuki Koike; Yasushi Miki, all of Tsukuba (JP)

(73) Assignee: Mitsubishi Gas Chemical Company, Inc., Tokyo (JP)

( * ) Notice: Under 35 U.S.C. 154(b), the term of this patent shall be extended for 0 days.

(21) Appl. No.: 09/340,021

(22) Filed: Jun. 28, 1999

(30) Foreign Application Priority Data

Jun. 26, 1998 (JP) .................................................. 10-180897

(51) Int. Cl.[7] .................................................. C07C 209/00
(52) U.S. Cl. .......................................... 564/479; 564/480
(58) Field of Search ...................................... 564/479, 480

(56) References Cited

U.S. PATENT DOCUMENTS

| 4,973,792 | 11/1990 | Lewis et al. . |
| 5,417,949 | * 5/1995 | McWilliams et al. ............ 423/239.2 |

FOREIGN PATENT DOCUMENTS

| DD 289 478 A5 | 5/1991 | (DE) . |
| 0 324 267 A1 | 7/1989 | (EP) . |
| WO 95/18675 | 7/1995 | (WO) . |

\* cited by examiner

*Primary Examiner*—Samuel Barts
(74) *Attorney, Agent, or Firm*—Pillsbury Madison & Sutro LLP

(57) ABSTRACT

Methylamines are prepared from methanol and ammonia in the presence of modified molecular sieve catalysts obtained by mixing crystalline molecular sieves such as SAPO with modifiers such as titanium oxide. The catalysts are also suitably used for a disproportionation reaction of monomethylamine.

6 Claims, No Drawings

CATALYSTS FOR PRODUCING METHYLAMINES AND METHODS FOR PRODUCING METHYLAMINES USING THE SAME

BACKGROUND OF THE INVENTION

1. Field of the Invention

The present invention relates to modified molecular sieve catalysts which are useful in an amination reaction of alcohols, typically for the production of methylamines from methanol and ammonia, and to methods for producing methylamines using said modified molecular sieve catalysts.

Among alkylamines obtained by the amination reaction of alcohols, methylamines are commercially important products having broad demands as materials for solvents, rubber products, pharmaceuticals and surfactants.

2. Description of the Prior Art

Methylamines are produced usually from methanol and ammonia using solid acid catalysts such as silica-alumina, at a temperature around 400° C. As generally known, the production in the presence of such silica-alumina catalysts is conducted under thermodynamic equilibrium. The main product is trimethylamine which has the least demand among the three amines. Dimethylamine is the most useful. Accordingly, methods for selectively producing dimethylamine in an amount exceeding the thermodynamic proportion have been developed. For example, there are methods using zeolites, such as zeolite A (JP 56-69846 A), FU-1 (JP 54-148708 A), ZSM-5 (U.S. Pat. No. 4,082,805), ferrierite and erionite (JP 56-113747 A), ZK-5, Rho, chabazite and erionite (JP 61-254256 A) and mordenite (JP 56-46846 A, JP 58-49340 A, JP 59-210050 A and JP 59-227841 A). These methods apply, to zeolites having small pore size, ion exchange, a de-aluminum treatment, steam treatment, addition of particular elements, silane-treatment and/or the other well known methods for controlling pore-sizes or modifying outer surfaces of zeolites. They intend to improve form-selectivity for dimethylamine and catalyst activity.

In addition, there is a method for producing monomethylamine in an amount exceeding the thermodynamic equilibrium proportion, by using silicoaluminophosphates, non-zeolite molecular sieves (JP 2-734 A).

The present inventors filed a patent application, on the basis of findings that silica-modified silicoaluminophosphates have a high activity together with a high selectivity for dimethylamine, as compared with prior arts in producing methylamines using zeolite catalysts (JP Application No. 9-197232).

SUMMARY OF THE INVENTION

In the known methods, modification of crystalline molecular sieve catalysts is an important and almost essential procedure in order to improve their activities and selectivities. A method of JP 6-75678 B, for example, mentions a modification by forming precipitations of silicon, aluminum, phosphorus or boron. JP 8-193057 A mentions a silylation by a silane treatment. However, these catalyst modification procedures are troublesome, and such catalyst modification processes are hardly simplified.

The present inventors have further studied to develop non-equilibrium type methylamine catalysts which are free from the disadvantages encountered in the conventional methylamine catalysts.

The present invention provides catalysts for producing methylamines. The catalysts are prepared by mixing a crystalline molecular sieve with one or more members of modifiers selected from the group consisting of titanium oxide, lanthanum oxide, zirconium oxide, yttrium oxide, cerium oxide, thorium oxide, niobium oxide, chromium oxide, molybdenum oxide, ruthenium oxide, rhenium oxide, iron oxide, cobalt oxide, palladium oxide, copper oxide, zinc oxide, gallium oxide, indium oxide, tin oxide, bismuth oxide, nickel oxide, manganese oxide, kaolinite, dickite, nacrite, halloysite, montmorillonite, talc, mica and illite. It further provides a method for producing methylamines from methanol and ammonia in the presence of the catalysts mentioned above. It also provides a method for producing dimethylamine from monmethylamine in the presence of the catalysts mentioned above.

When methylamines are produced from methanol and ammonia using the catalysts according to the invention, conversion of methanol is large and a satisfactory selectivity is obtained wherein a much more amount of dimethylamine and a less amount of trimethylamine are produced. In addition, excellent catalyst activities are sustained for a long period of time. The catalysts according to the invention can be prepared by a simple procedure in which a crystalline molecular sieve is mixed with a modifier such as the oxides mentioned above, followed by calcination, if required, and the mixture is extruded, compressed, or pelletized for shaping.

DESCRIPTION OF THE PREFERRED EMBODIMENTS

Preferable structures of the crystalline molecular sieves of the present invention are those having effective micropore size ranging from 0.3 to 0.6 nm. According to the IUPAC structural code of zeolites and their analogous compounds, for example, 8-membered ring-structural ABW, AEI, AFX, APC, ATN, ATT, ATV, AWW, CHA, DDR, EAB, ERI, GIS, JBW, KFI, LEV, LTA, MER, MON, PAU, PHI, RHO, RTE, RTH and VNI; 9-membered ring-structural CHI, LOV, RSN and VSV; 10-membered ring-structural DAC, EPI, FER, LAU, MEL, MFI, MFS, MTT, NES, TON and WEI; and 12-membered ring-structural AFS, AFY, ATO, CAN, GME, MAZ, MEI, MTW, OFF, RON and VET; and the like, are mentioned. The crystalline molecular sieves of the present invention also include crystalline silicoaluminophosphates and crystalline aluminosilicates.

The crystalline silicoaluminophosphates used in the present invention are so-called SAPO. They are prepared by an isomorphic replacement of a part of P or Al—P bonds with Si, in a crystalline aluminum phosphate compound (ALPO) having a chemical composition of the formula 1:

$$Al_2O_3 \cdot (1.0 \pm 0.2) P_2O_5 \tag{1}$$

which is represented by oxide mole ratios, excluding crystalline water and organic bases of structure directing agents (for example, JP 57-77015 A). Such crystalline silicoaluminophosphates include, for example, SAPO-5, 11, 17, 18, 31, 34, 35, 37, 40, 41, 42, 43, 44, 47 and 56, RUW-18, UTD-2, 3, 5 and 6, and those prepared from these compounds by an isomorphic replacement with Li, Ti, Zr, V, Cr, Mn, Fe, Co, Zn, Be, Mg, Ca, B, Ga, Ge, or the like. Herein, the relationship between the SAPO numbers and their structures is mentioned in, for example, Encyclopedia of Inorganic Chemistry, Vol. 8, 4369 (1994). The crystalline silicoaluminophosphates may be of H-type or those in which a part of the H-type has been replaced with an atom selected from Li, Ti, Zr, V, Cr., Mn, Fe, Co, Zn, Be, Mg, Ca, B, Ga and Ge. These crystalline silicoaluminophosphates can readily be prepared using an aluminum compound, an aqueous phosphoric acid solution, and an Si-source agent, together with an amine or quaternary ammonium compound as a structure directing agent. In order to prepare the crystalline silicoaluminophosphates, there are already known methods as described in, for example, JP 59-35018 A and the other improved methods. As the crystalline aluminosilicates of the present invention, there are, for example, chabazite, mordenite, erionite, ferrierite, offretite, gmelinite, paulingite, clinoptilolite, epistilbite, phillipsite, levynite, zeolite-A, rho, ZK-5, EU-1, FU-1, ZSM-5, 11, 12, 20, 22 and 23, and NU-3. Among these crystalline molecular sieves, crystalline silicoaluminophosphates, mordenite and chabazite are preferably used, because of their higher catalytic activities which are sustained for a longer period of time.

Each of the crystalline molecular sieves may be used singly or as mixtures of them. They may be not only as a simple mixture of them, but as an intergrowth, for example, of offretite and erionite as in U.S. Pat. No. 4,086,186, namely an intergrowth of two kinds of crystalline molecular sieves having different topologies from each other.

These crystalline molecular sieves may be subjected to ion-exchange or metal replacement, in order to intensify the acidity or activity. To this effect, are adequately used Li, Na, K, Rb, Cs, Be, Mg, Ca, Sr, Ba, Ga, Zn, Fe, Co, B, P, Ge or others.

Modifiers used for the preparation of the present catalysts are, for exampe, titanium oxide, lanthanum oxide, zirconium oxide, yttrium oxide, cerium oxide, thorium oxide, niobium oxide, chromium oxide, molybdenum oxide, ruthenium oxide, rhenium oxide, iron oxide, cobalt oxide, palladium oxide, copper oxide, zinc oxide, gallium oxide, indium oxide, tin oxide, bismuth oxide, nickel oxide, manganese oxide, kaolinite, dickite, nacrite, halloysite, montmorillonite, talc, mica and illite. At least one of them is used for the modification of the crystalline molecular sieves. Among them, zirconium oxide, yttrium oxide or titanium oxide is preferably used, because they bring about higher catalytic activities which are sustained for a longer period of time. When two or more kinds of the modifiers are used, they may be used as simple mixtures, or as multiple oxide mixtures prepared according to a heterogeneous or homogeneous coprecipitation process. For example, there may be mentioned titanium oxide-zirconium oxide, titanium oxide-tin oxide and the like. Other double oxides of spinel, inverse-spinel, ilmenite or perovskite structures may be used, such as barium zirconate, silicon zirconate, strontium zirconate, calcium stannate, cadmium stannate, lithium niobate, potassium niobate, barium titanate, iron titanate, cobalt titanate, nickel titanate, magnesium titanate and the like.

Mixing crystalline molecular sieves and modifiers according to the present invention may be effected by first preparing powder mixtures uniformly dispersed, for example, through mechanical shaking. The powdered materials are usually mixed. Alternatively, impregnation mixing or dispersion mixing may be effected using a liquid material in order to obtain homogeneous mixtures. In the latter case, drying and calcination steps are followed. An amount of the modifiers to be added may generally be not more than 50% by weight in terms of oxide per weight of the molecular sieve. Too much amount of modifiers tends to impair the effectiveness. An amount of not more than 20% by weight is preferable, particularly, 1 to 10% by weight being more preferable. In cases where modifiers containing a small amount of Au, Ag, Pt, Pd, Ni or Co are used for the purpose of fine reforming of the catalysts, an amount of not more than 5% by weight is preferable.

Binders such as silica and alumina may be mixed before shaping of the present catalyst. However, such binders are not always necessary, since the modifiers themselves often act as binders in the present invention. No binders are every so often used.

Calcining may be carried out before the shaping step. However, the calcination is not always necessary, either, since the present catalysts are well active even without such a calcination step.

Mixtures of the crystalline molecular sieves and modifiers are shaped by extrusion, compression molding or pelletization, according to conventional procedures. The catalysts thus prepared are effectively act as a complex form of the crystalline molecular sieves and the oxides. Lubricants may preferably be used in the shaping step in order to facilitate release of the catalyst. They include graphite, metal salts of stearic acid such as zinc stearate, magnesium stearate, lithium stearate, calcium stearate or the like, talc, mica, fumed silica, Teflon or other organic fluorine compounds, or silicones or the like.

The present modified molecular sieve catalysts are suitably used for a production of melthylamines in amination of alcohols, or for a production of dimethylamine through a disproportionation reaction of monomethylamine.

Hereinafter, preferable conditions are mentioned in respect to the production of methylamines using the present modified molecular sieve as a catalyst for amination of alcohols. The reaction is conducted, preferably, but not exclusively, in a flowing system on a gaseous fixed bed or fluidized bed. One of the starting materials is alcohols having 1 to 3 carbon atoms, specifically, methanol, ethanol or 1-propanol. The methanol may contain some amount of dimethyl ether. Another material is ammonia, in which amines may be contained, corresponding to the alcohol reactant moiety, such as methylamines, ethylamines, propylamines and the like. An amount ratio of ammonia to the alcohols is preferably 0.5 to 20, more preferably 1 to 5, in mole. Reaction pressure is preferably 0.1 to 10 MPa, more preferably 0.5 to 2 MPa. Reaction temperature is preferably 200 to 400° C., more preferably 250 to 360° C. So far as material feeding velocity (space velocity, GHSV) is concerned, the larger, the better from a view point of the productivity. However, too large velocity unfavorably decreases conversion ratio of materials. Thus, a space velocity of 100 to 10,000 per hour is preferable.

The present modified molecular sieve catalysts are also suitably used for a disproportionation reaction of monomethylamine. In this reaction, the monomethylamine may contain a small amount of other amines, methanol and/or dimethyl ether. The same pressure and temperature conditions as in the amination reaction of alcohols can be used.

As mentioned in detail above, the catalysts according to the invention are useful for the amination reaction. They are also useful as catalysts for other chemical reactions, such as alkylation, disproportionation, hydrogenation cracking and other crackings, reforming, isomerization, hydrogenation, dehydrogenation, oxidation, reduction, dehydration, polymerization or others. All we have to do is to simply modify the molecular sieve catalysts according to the field of arts. There are effective atoms as catalyst, in each chemical reaction. For example, Ni, Pt and Pd are effective atoms for hydrogenation reaction.

Mechanism of the large activity and excellent selectivity of the present catalysts in the methylamine production, particularly in the amination reaction of alcohols, has not yet been clear, but it may be due to synergistic effect from the crystalline molecular sieves and the oxide modifers.

EXAMPLES

The invention will more fully be explained referring to reactions between methanol and ammonia, and disproportionation reactions of monomethylamine. In these examples, reactions were conducted in flowing reaction apparatus provided with material tanks, material feeding pumps, inert gas charging devices, reaction tubes (inner diameter of 13 Ø, length of 300 mm, made of SUS 316L), sampling tanks, back pressure valves, etc. After 5 hour steady reaction flow, the product sample was taken over about 1 hour, analyzed by gas chromatography to obtain the composition distribution. The silicoaluminophosphates (SAPOs) used for the catalyst preparation were commercial products of NIKKI-Universal Co., Japan.

(Reactions of Methanol and Ammonia)

Examples 1 to 5

SAPO-34s were mixed with 5% by weight of montmorillonite (bentonite), kaolinite, titanium oxide, zirconium oxide and yttrium oxide, as modifiers, respectively. The mixtures were uniformly dispersed in water. Then, the mixtures were dried at 120° C. for 6 hours, calcined at 500° C. for 3 hours, and shaped by compression to prepare catalysts, respectively. The catalyst each was filled in the reaction tube as mentioned above, to which a gaseous mixture of methanol and ammonia (weight ratio, 1:1) was introduced at a space velocity of 1500 $h^{-1}$ to effect a reaction of methanol and ammonia at 320° C. The results are shown in Table 1.

Examples 6 to 25

Example 1s were repeated except that catalysts were used wherein mordenite, ZSM-5, ferrierite and chabazite, were used, respectively, in place of the montmorillonite and the others mentioned in Examples 1–5. The results are shown in Table 1.

Comparative Example 1

Example 1 was repeated except that a catalyst was used wherein no modifier was mixed with SAPO-34. The results are shown in Table 1.

Comparative Examples 2 to 5

Example 1s were repeated except that catalysts were used wherein no modifiers were added to equilibrium-type silica-alumina, mordenite, SAPO-11 and CoSAPO-34, respectively. The CoSAPO-34 used in Comparative Example 5 is a crystalline silicoaluminophosphate in which a part of H-type has been replaced by Co. The results are shown in Table 1.

(Disproportionation Reaction of Monomethylamine)

Example 26

Zirconium oxide-modified SAPO-34 prepared in the same way as in Example 4 was filled in a reaction tube, to which was introduced a methylamine gas at a space velocity of 1500 $h^{-1}$ to effect a disproportionation reaction of methylamine at 320° C. The results are shown in Table 1.

Comparative Example 6

Example 26 was repeated except that the catalyst prepared in Comparative Example 1 was used in place of the zirconium oxide-modified SAPO-34. The results are shown in Table 1.

Example 27

Zirconium oxide-modified SAPO-34 prepared as in Example 4 was filled in the reaction tube, to which a gaseous mixture of methanol and ammonia (weight ratio, 1:1) was fed to cause a reaction of methanol and ammonia at 320° C. for 150 hours. At this time, the normal space velocity of 1500 $h^{-1}$ was increased to 2500 $h^{-1}$. The catalyst activities were measured 10 hours and 150 hours after the commencement of the reaction. This is an accelerated catalyst life test, in which a space velocity of 2500 $h^{-1}$ corresponds to about 10 times accelerated condition, as compared to that of 1500 $h^{-1}$. The results are shown in Table 2.

Example 28

The accelerated catalyst life test was conducted in the same manner as in Example 27 except that a yttrium oxide-modified SAPO-34 catalyst prepared as in Example 5 was used. The results are shown in Table 2.

Example 29

The accelerated catalyst life test was conducted in the same manner as in Example 27 except that a titanium oxide-modified SAPO-34 catalyst prepared as in Example 3 was used. The results are shown Table 2.

Example 30

The accelerated catalyst life test was conducted in the same manner as in Example 27 except that a lanthanum oxide-modified SAPO-34 catalyst was used. The catalyst had been prepared in the same way as in Example 1 except that 5% by weight of lanthanum oxide was used as a modifier. The results are shown in Table 2.

Comparative Example 8

The accelerated catalyst life test was conducted in the same manner as in Example 27 except that a catalyst prepared as in Comparative Example 1 (no modifier) was used. The results are shown in Table 2.

Comparative Example 9

The accelerated catalyst life test was conducted in the same manner as in Example 27 except that a silane-treated SAPO-34 catalyst containing no modifier, prepared in the same procedures as in Example 1, was used. The results are shown in Table 2.

Comparative Example 10

The accelerated catalyst life test was conducted in the same manner as in Example 27 except that a catalyst of SAPO-34 mixed with 5% by weight of powdered silica as a modifier, prepared in the same procedures as in Example 1, was used. The results are shown in Table 2.

Example 31

The accelerated catalyst life test was conducted in the same manner as in Example 27 except that a zirconium oxide-modified mordenite catalyst prepared as in Example 13 was used. The results are shown in Table 2.

Comparative Example 11

The accelerated catalyst life test was conducted in the same manner as in Example 27 except that a mordenite catalyst containing no modifier, prepared in the same procedures as in Example 1, was used. The results are shown in Table 2.

Comparative Example 12

The accelerated catalyst life test was conducted in the same manner as in Example 27 except that a mordenite catalyst containing 5% by weight of powdered silica as a modifier, prepared in the same procedures as in Example 1, was used. The results are shown in Table 2.

Examples and Comparative Examples show that the present catalysts are obtained by relatively simple procedures. The amination reactions of alcohols such as a reaction of methanol and ammonia are conducted controlling production of trimethylamine as small as possible. The catalysts have excellent conversion and large selectivity keeping high activities for a long period of time.

TABLE 1

(Results of reactions in Example)

| | Molecular sieves | Modifiers | Amount added wt. % | Temp. °C. | Conversion ratio per MeOH, % | Selectivity (wt. %) | | |
|---|---|---|---|---|---|---|---|---|
| | | | | | | MMA | DMA | TMA |
| Ex. 1 | SAPO-34 | montmorillonite | 5 | 320 | 98.4 | 28 | 45 | 27 |
| Ex. 2 | " | kaolinite | 5 | 320 | 98.5 | 33 | 57 | 10 |
| Ex. 3 | " | titanium oxide (rutile) | 5 | 320 | 98.6 | 36 | 59 | 5 |
| Ex. 4 | " | zirconium oxide | 5 | 320 | 98.8 | 35 | 62 | 3 |
| Ex. 5 | " | yttrium oxide | 5 | 320 | 98.8 | 35 | 63 | 2 |
| Ex. 6 | mordenite | kaolinite | 5 | 320 | 97.6 | 35 | 60 | 5 |
| Ex. 7 | " | yttrium oxide | 5 | 300 | 98.5 | 35 | 60 | 5 |
| Ex. 8 | " | lanthanum oxide | 5 | 300 | 95.5 | 33 | 60 | 7 |
| Ex. 9 | " | cerium oxide | 5 | 300 | 94.4 | 33 | 60 | 7 |
| Ex. 10 | " | thorium oxide | 5 | 300 | 93.1 | 33 | 60 | 7 |
| Ex. 11 | " | magnesium oxide | 5 | 300 | 86.1 | 33 | 59 | 8 |
| Ex. 12 | " | barium oxide | 5 | 300 | 92.1 | 36 | 57 | 7 |
| Ex. 13 | " | zirconium oxide | 5 | 300 | 98.8 | 36 | 61 | 5 |
| Ex. 14 | " | chromium oxide | 5 | 300 | 96.8 | 36 | 60 | 4 |
| Ex. 15 | " | niobium oxide | 5 | 300 | 96.0 | 32 | 60 | 8 |
| Ex. 16 | " | tin oxide | 5 | 300 | 96.2 | 32 | 61 | 7 |
| Ex. 17 | " | indium oxide | 5 | 300 | 96.6 | 32 | 62 | 6 |
| Ex. 18 | " | iron oxide | 5 | 300 | 98.1 | 36 | 59 | 5 |
| Ex. 19 | " | cobalt oxide | 5 | 300 | 94.1 | 32 | 59 | 9 |
| Ex. 20 | " | nickel oxide | 5 | 300 | 96.0 | 33 | 60 | 7 |
| Ex. 21 | " | zinc oxide | 5 | 300 | 78.1 | 40 | 58 | 2 |
| Ex. 22 | " | palladium oxide | 1 | 300 | 96.0 | 33 | 61 | 2 |
| Ex. 23 | ZSM-5 | zirconium oxide | 5 | 320 | 98.1 | 27 | 48 | 25 |
| Ex. 24 | ferrierite | zirconium oxide | 5 | 320 | 88.6 | 30 | 42 | 28 |
| Ex. 25 | chabazite | zirconium oxide | 5 | 340 | 97.6 | 36 | 60 | 4 |
| Comp. Ex. 1 | SAPO-34 | | 0 | 320 | 83.0 | 30 | 30 | 40 |
| Comp. Ex. 2 | equilibrium-type silica-alumina | | 0 | 400 | 99.9 | 24 | 25 | 51 |
| Comp. Ex. 3 | mordenite | | 0 | 320 | 88.5 | 28 | 30 | 42 |
| Comp. Ex. 4 | SAPO-11 | | 0 | 320 | 47.0 | 28 | 30 | 42 |
| Comp. Ex. 5 | CoSAPO-34 | | 0 | 320 | 88.0 | 33 | 30 | 34 |

(disproportionation reaction of monomethylamine)

| | Molecular sieves | Modifiers | Amount added wt. % | Temp. °C. | MMA conversion ratio, % | Selectivity (wt. %) | |
|---|---|---|---|---|---|---|---|
| | | | | | | DMA | TMA |
| Ex. 26 | SAPO-34 | Zirconium oxide | 5 | 320 | 80.0 | 98 | 2 |
| Comp. Ex. 6 | SAPO-34 | | 0 | 320 | 67.5 | 90 | 10 |

Space velocity: Reaction of methanol and ammonia, 1500 h$^{-1}$ Disproportionation reaction of monomethylamine, 1500 h$^{-1}$

TABLE 2

Catalyst life tests

| Catalysts | | Temp. °C. | SV h$^{-1}$ | Conversion ratio (%) at catalyst life tests | |
|---|---|---|---|---|---|
| | | | | 10 h* | 150 h* |
| Ex. 27 | zirconium oxide-modified SAPO-34 | 320 | 2500 | 98.2 | 94.6 |
| Ex. 28 | yttrium oxide-modified SAPO-34 | 320 | 2500 | 98.5 | 94.0 |
| Ex. 29 | titanium oxide-modified SAPO-34 | 320 | 2500 | 98.2 | 94.2 |
| Ex. 30 | lanthanum oxide-modified SAPO-34 | 320 | 2500 | 97.6 | 91.0 |
| Comp. Ex. 8 | SAPO-34 | 320 | 2500 | 98.6 | 73.0 |
| Comp. Ex. 9 | silica-modified SAPO-34 by silane-treatment | 320 | 2500 | 96.8 | 75.0 |
| Comp. Ex. 10 | silica-modified SAPO-34 by adding powd. silica | 320 | 2500 | 96.2 | 88.3 |
| Ex. 31 | zirconium oxide-modified mordenite | 320 | 2500 | 96.2 | 92.4 |
| Comp. Ex. 11 | mordenite | 320 | 2500 | 96.8 | 76.5 |
| Comp. Ex. 12 | silica-modified mordenite by adding powd. silica | 320 | 2500 | 96.2 | 86.4 |

*Period of time after the commencement of reaction

What is claimed is:

1. A method for producing methylamines from methanol and ammonia which comprises conducting the reaction in the presence of a catalyst for producing methylamines, said catalyst comprising a crystalline molecular sieve mixed with at least one member selected from the group consisting of titanium oxide, lanthanum oxide, zirconium oxide, yttrium oxide, cerium oxide, thorium oxide, niobium oxide, chromium oxide, molybdenum oxide, ruthenium oxide, rhenium oxide, iron oxide, cobalt oxide, palladium oxide, copper oxide, zinc oxide, gallium oxide, indium oxide, tin oxide, bismuth oxide, nickel oxide, manganese oxide, kaolinite, dickite, nacrite, halloysite, montmorillonite, talc, mica and illite, as a modifier which is 50% by weight or less in terms of oxide on the basis of the molecular sieve.

2. A method for producing dimethylamine from monomethylamine which comprises conducting the reaction in the presence of a catalyst for producing methylamines said catalyst comprising a crystalline molecular sieve mixed with at least one member selected from the group consisting of titanium oxide, lanthanum oxide, zirconium oxide, yttrium oxide, cerium oxide, thorium oxide, niobium oxide, chromium oxide, molybdenum oxide, ruthenium oxide, rhenium oxide, iron oxide, cobalt oxide, palladium oxide, copper oxide, zinc oxide, gallium oxide, indium oxide, tin oxide, bismuth oxide, nickel oxide, manganese oxide, kaolinite, dickite, nacrite, halloysite, montmorillonite, talc, mica and illite, as a modifier which is 50% by weight or less in terms of oxide on the basis of the molecular sieve.

3. The method for producing methylamines according to claim 1, wherein the crystalline molecular sieve is crystalline silicoaluminophosphate, mordenite or chabazite.

4. A method for producing methylamines according to claim 1, wherein the modifier is zirconium oxide, yttrium oxide or titanium oxide.

5. A method for producing dimethylamines according to claim 2, wherein the crystalline molecular sieve is crystalline silicoaluminophosphate, mordenite or chabazite.

6. A method for producing diemethylamines according to claim 2, wherein the modifier is zirconium oxide, yttrium oxide or titanium oxide.

* * * * *